US005371002A

United States Patent [19]

Dennis et al.

[11] Patent Number: 5,371,002
[45] Date of Patent: Dec. 6, 1994

[54] METHOD OF PRODUCTION OF POLY-BETA-HYDROXYALKANOATE COPOLYMERS

[75] Inventors: Douglas E. Dennis, Weyers Cave, Va.; Steven C. Slater, Cleveland Heights, Ohio

[73] Assignee: James Madison University, Harrisonburg, Va.

[21] Appl. No.: 767,008

[22] Filed: Sep. 27, 1991

Related U.S. Application Data

[63] Continuation-in-part of Ser. No. 362,514, Jun. 7, 1989, and a continuation-in-part of Ser. No. 528,549, May 25, 1990.

[51] Int. Cl.⁵ .......................... C12P 7/44; C12P 7/52; C12N 15/31; C12N 1/21
[52] U.S. Cl. ..................... 435/142; 435/141; 435/172.3; 435/252.33
[58] Field of Search ............ 435/141, 172.3, 252.33, 435/142

[56] References Cited

FOREIGN PATENT DOCUMENTS 0052459 5/1982 European Pat. Off. .

OTHER PUBLICATIONS

Slater, et al., American Society for Microbiology, Annual Meeting, Mar. 1–6, 1987, Abstract H-123.
Slater et al., Virginia Journal of Science, p. 152, May 19–22, 1987.
Johnson, et al., Virginia Journal of Science, p. 150, May 19–22, 1987.
Brown, et al., Journal of General Microbiology, vol. 102, pp. 327–336, 1977.

*Primary Examiner*—George C. Elliott
*Attorney, Agent, or Firm*—Seed and Berry

[57] ABSTRACT

The invention related to recombinant deoxyribonucleic acid (DNA) technology and, more particularly, to a process whereby polybeta-hydroxyalkanoate (PHA) copolymers can be synthesized in a recombinant host strain containing the poly-beta-hydroxybutyrate (PHB) biosynthetic genes of *Alcaligenes eutrophus*.

8 Claims, 14 Drawing Sheets

Analysis of cosmid clones for enzyme activity and PHB accumulation

| Bacterium[a] | Cosmid | β-Ketothiolase activity[b] | Acetoacetyl-CoA reductase activity[c] | mg of PHB/ml of culture | %PHB |
|---|---|---|---|---|---|
| E. coli LE392 | None | 0.0 | 0.0 | 0.0 | 0 |
| A. eutrophus H16 | None | 12.4 | 12.3 | 1.18 | 35 |
| E. coli LE392 | pAE65 | 5.2 | 39.0 | 0.03 | 1 |
| E. coli LE392 | pAE175 | 16.2 | 0.2 | 0.47 | 16 |
| E. coli LE392 | pAE537 | 2.4 | 0.0 | 0.0 | 0 |
| E. coli LE392 | pAE683 | 10.4 | 0.0 | 0.0 | 0 |
| E. coli LE392 | pAE689 | 14.8 | 0.2 | 0.64 | 20 |
| E. coli LE392 | pAE902 | 8.5 | 0.0 | 0.0 | 0 |

[a] Bacteria were grown in LB plus 1% gluconate.
[b] Micromoles of acetoacetyl-CoA degraded per minute per milligram of protein.
[c] Micromoles of NADPH reduced per minute per milligram of protein.

FIG. 2

Analysis of subclones for enzyme activity and PHB production

| Bacterium[a] | Plasmid | β-Ketothiolase activity[b] | Acetoacetyl-CoA reductase activity[c] | mg of PHB/ml of culture | %PHB |
|---|---|---|---|---|---|
| E. coli LE392 | None | 0.0 | 0.0 | 0.0 | 0 |
| A. eutrophus H16 | None | 3.5 | 11.2 | 1.64 | 49 |
| E. coli LE392 | pAE175 | 1.7 | 1.2 | 0.71 | 19 |
| E. coli DH5 | pBK6 | 1.6 | 0.0 | 0.0 | 0 |
| E. coli DH5 | pBK12 | 2.0 | 4.5 | 0.71 | 18 |
| E. coli DH5 | pSB2 | 0.0 | 0.0 | 0.0 | 0 |
| E. coli DH5 | pSB3 | 0.0 | 0.0 | 0.0 | 0 |
| E. coli DH5 | pSB8 | 59.2 | 50.1 | 0.0 | 0 |
| E. coli DH5 | pSB9 | 20.2 | 8.7 | 0.0 | 0 |
| E. coli DH5 | pSB13 | 0.0 | 0.0 | 0.0 | 0 |
| E. coli DH5 | pSB14 | 0.0 | 0.0 | 0.0 | 0 |
| E. coli DH5 | pSB20 | 2.7 | 0.7 | 2.82 | 54 |
| E. coli DH5 | pSB21 | 2.4 | 0.6 | 2.28 | 39 |

[a] For enzyme assays, bacteria were grown in LB. For the PHB assay, bacteria were grown in LB plus 1% gluconate.
[b] Micromoles of acetoacetyl-CoA degraded per minute per milligram of protein.
[c] Micromoles of NADPH reduced per minute per milligram of protein.

FIG. 4

| Strain | Medium | OD-600 | PHB | PHV |
|---|---|---|---|---|
| 5218 | 40 mM Ac/10 mM Prop | 2.62 | 0 | 0 |
| 5218 | 40 mM Ac/10 mM Prop/0.4% glu | 8.18 | 292,000 | 31,000 |
| 5218 | 20 mM Ac/25 mM Prop/0.4% glu | 7.46 | 169,000 | 64,000 |
| 5218 | 10 mM Ac/10 mM Prop/0.4% glu | 6.28 | 77,000 | 52,000 |
| 5218 | 25 mM Ac/0.4% glu | 8.02 | 327,000 | 0 |
| 5218 | 25 mM prop/0.4% glu | 5.88 | 99,000 | 63,000 |
| HMS174/p4a | 20 mM Ac/25 mM prop/0.4% glu | 5.56 | 120,000 | 0 |
| HMS174/p4a | 25 mM prop/0.4% glu | 3.46 | 14,000 | 0 |

FIG. 11

METHOD OF PRODUCTION OF POLY-BETA-HYDROXYALKANOATE COPOLYMERS

This is a continuation-in-part of copending U.S. Ser. No. 07/362,514 filed Jun. 7, 1989, which is expressly incorporated herein by reference, and is also a continuation-in-part of U.S. Ser. No. 07/528,549 filed May 25, 1990, which is expressly incorporated herein by reference.

TECHNICAL FIELD

The invention is generally related to recombinant deoxyribonucleic acid (DNA) technology and, more particularly, to cloning the genes responsible for biosynthesis of poly-betahydroxyalkanoates (PHA) from *Alcaligenes eutrophus* H16 (*A. eutrophus*) into *Escherichia coli* (*E. coli*) and expressing the PHA's biosynthetic pathway in *E. coli*.

In particular, the invention is related to a process whereby poly-betahydroxyalkanoate (PHA) copolymers comprising, for example, poly-betahydroxybutyrate (PHB) and poly-betahydroxyvalerate (PHV) can be synthesized in a recombinant strain of *Escherichia coli* containing the PHB biosynthetic genes of *Alcaligenes eutrophus*.

BACKGROUND ART

Poly-beta-hydroxyalkanoates (PHA's) are a heterogeneous family of biodegradable aliphatic polyesters Which include, for example, derived polymers such as poly-beta-hydroxybutyrate (PHB) and poly-beta-hydroxyvalerate (PHV).

PHB is an energy storage material produced by a variety of bacteria in response to environmental stress. Lemoigne discovered the presence of PHB in Bacillus in 1926 and it has since been identified in many different bacterial genera, including *Azotobacter beijerinckia*, *Alcaligenes*, *Pseudomonas*, *Rhizobium*, and *Rhodospirillum*. PHB is a homopolymer of D-(−)-3-hydroxybutyrate and has physical properties comparable to polypropylene. The biodegradability of PHB makes it especially suitable for a wide variety of purposes. PHB has also been used as a source of chiral centers for the organic synthesis of certain antibiotics, and has been utilized in drug delivery and bone replacement applications.

The biosynthesis of PHB has been studied extensively in *A. eutrophus* and *Azotobacter beijerinckii*. FIG. 1 outlines a three step biosynthetic pathway for PHB found in many prokaryotic organisms. Beta-ketothiolase first catalyzes the reversible condensation of two acetyl coenzyme A (CoA) molecules to acetoacetyl-CoA. The acetoacetyl-CoA is reduced by acetoacetyl-CoA reductase to D-(−)-3-hydroxybutyryl-CoA. Enzyme action of the acetoacetyl-CoA reductase is dependent on NADPH. PHB synthetase polymerizes the D-(−)-3-hydroxybutyryl-CoA to PHB.

PHB accumulates when growth of a bacteria culture is restricted by a nutrient other than a carbon source. For example, oxygen deprivation, nitrogen deprivation, sulfate limitation and magnesium limitation have all been used as limitations on environmental conditions. Under such environmental conditions, the PHB content in bacteria cells can increase to as much as 80% of the dry weight. When the limiting conditions are relaxed, PHB quantities decrease to preinduction levels. Induction studies have revealed that both beta-ketothiolase and acetoacetyl CoA reductase enzymatic activities increase markedly in response to PHB-stimulating limitation conditions.

It is now widely known that PHB can be accumulated in natural bacteria genera (for example, *Alcaligenes eutrophus*) using a wide variety of biotechnological processes and extraction methods. In addition, it has recently been known that PHA copolymers of PHB and PHV can be produced using various natural bacterial genera. One example of such copolymers is the subject of U.S. Pat. No. 4,876,331 to Doi and assigned to Mitsubishi Kasei Corporation. Another example of such copolymers is commercially available under the Biopol R trademark from Imperial Chemical Industries.

While PHA's can be produced in natural bacterial genera, these bacteria are less manipulatable and not as well characterized as *E. coli*. In the field of genetic engineering, a relatively large body of knowledge exists for *E. coli*. *E. coli* have been utilized as host cells for producing a wide variety of products including Human Growth Hormone, insulin and interferon.

The Slater et al., J. Biol. 170:4431 (October 1988) and the patent applications filed Jun. 7, 1989, Ser. No. 07/528,549, filed May 25, 1990 and Ser. No. 07/705,806, filed May 24, 1991, all of which are expressly incorporated herein by reference, describe the cloning of the PHB biosynthetic pathway from *A. eutrophus* into *E. coli*. The cloning of the PHB biosynthetic pathway into *E. coli* has also been later described by Schubert et al., J. Bacter. 170:5837 (December 1988); Peoples, et al., J. Biol. Chem., 264:15298 (Sept. 1989a) and Peoples et al., J. Biol. chem., 264:15293 (Sept. 1989b). There are several decided advantages of producing PHB by transformed *E. coli* over the production of PHB in *A. eutrophus*. First, the reproductive potential of *E. coli* is extremely high so that in a fermentation situation, it is possible to grow *E. coli* cells to a high concentration of biomass more quickly. Second, the accumulation of PHB in *E. coli* occurs to substantially higher levels than it does in *A. eutrophus*. The accumulation of PHB in *E. coli* (wt. of PHB/dry cell weight) as high as 95% has been obtained using the invention disclosed in the aboveidentified parent applications while highest accumulation of PHB in *A. eutrophus* is only around 80%. Third, since the PHB biosynthetic pathway is cloned on a plasmid, it is possible to make mutants that are even more efficient at PHB production than those disclosed in the above-identified patent applications. Fourth, *E. coli* enjoys the advantage of being able to use various different carbon sources. *A. eutrophus* does not possess this property. Lastly, *E. coli* is a well studied organism and there are a myriad of experimental techniques that can be used advantageously in other steps of PHB production. Thus, the prohibitive costs associated with *A. eutrophus*-produced PHB can be avoided such that it is commercially feasible to produce PHB on a large commercial scale.

The cloning of the PHB biosynthetic pathway found in *A. eutrophus* H16 into *E. coli* and expressing that pathway by the production of PHB in the cloned *E. coli* was disclosed in the parent Ser. No. 07/362,514 patent application. An *A. eutrophus* H16 library was constructed using cosmid pVK102. Cosmid clones that encoded the PHB biosynthetic pathway were sought by assaying for betaketothiolase. Six enzyme positive clones were identified and three of these clones manifested acetoacetyl CoA reductase activity and accumulated PHB. PHB was produced in the cosmid clones at approximately 50% of the level found *A. eutrophus*. One cosmid clone was subjected to subcloning experiments, and the PHB biosynthetic pathway was isolated on a 5.5 kilobase (kb) KpnI-EcoRI fragment, plasmid pSB20. This fragment can direct the synthesis of PHB in *E. coli* to levels approaching 50–55% of the bacterial cell dry weight.

A strain of *E. coli*, i.e., HMS174, has been transformed by a vector containing a plasmid (p4A) with the PHB biosynthetic pathway and approximately four hundred extra bases on both the upstream and downstream sides of the pathway. The HMS174 strain of *E. coli* contains a lactose utilization system and is recombination deficient so that a plasmid containing lactose genetic regions will not recombine and make the construct unstable. The strain of transformed *E. coli* can be grown in minimal media containing whey and has an average yield of PHB of approximately 85% (PHB dry weight/total cell dry weight).

However, until the present invention, it has been not possible to use the PHB transformed *E. coli* technology to produce PHA copolymers comprising PHB and other polymers. PHA's are generally defined by the carbon number of their backbone. For instance, the PHA that has a C4 backbone is poly-beta-hydroxybutyrate, whereas the PHA that has a C5 backbone is poly-beta-hydroxyvalerate. The size of the backbone has been shown to vary with the bacterial species and the carbon source. That is, certain species have only been shown to produce PHB, others produce PHB and PHV, still others produce PHA's such as poly-beta-hydroxydodecanoate. It is now understood that in order to produce PHA's having monomeric constituents higher than C4, there must be a carbon source in addition to/other than glucose. Thus, *Alcaligenes eutrophus* produces PHB when grown on glucose or gluconate, but produces PHB-co-V if valerate is added to the culture medium. Likewise, in order to induce *Pseudomonas fluorescens* to produce poly-beta-hydroxyoctanoate, the bacterium must be fed octane.

The importance of each PHA copolymer is that the plastic properties of each polymer vary considerably with the size of the carbon backbone of the monomer unit. PHB is considered to be a "brittle" plastic, whereas PHV is a more flexible plastic. In the same manner, poly-hydroxy-octanoate is a very flexible "rubbery" plastic.

This difference in plastic property allows PHB-co-V to be used in films, whereas PHB is not suited to plastic film applications, but more to molded products. Furthermore, the composition of the PHAs produced by bacteria can be varied by altering the culture conditions. In the case of *A. eutrophus*, valerate levels in the growing culture are altered to produce a PHB-co-V polymer that contains valerate monomer units of anywhere between 1% to 30% of the polymer. The flexibility of the copolymer increases as the percentage of valerate increases.

DESCRIPTION OF INVENTION

The present invention encompasses the production of PHA's by introducing a vector containing a DNA sequence coding for the polybeta-hydroxybutyrate biosynthetic pathway into a host which expresses the enzymes of acetate utilization. The host can express the enzymes of acetate utilization in different ways. For example, one way is to culture a host containing the DNA sequence for the PHB biosynthetic pathway on a first substrate which induces production of acetate utilization genes in the host. Thereafter the host is cultured on a second substrate comprising a carbon source. The host is cultured on the second substrate, during which time the host expresses the PHB biosynthetic pathway and the host produces PHB and another PHA copolymer. The PHA copolymers produced by the host are recovered using one or more of the various known methods for recovering PHB's from host cells.

Another way to produce PHA copolymers is to introduce a cosmid or a plasmid harboring the DNA sequence for the PHB biosynthetic pathway in a host which is either a mutant in acetate utilization or which expresses the acetate utilization genes constituitively. The resulting recombinant host is cultured in a substrate comprising a carbon source and propionate.

Various embodiments of the present invention include the cloning of the DNA sequence coding for PHB from *A. eutrophus* H16 carried on a p4A plasmid into *E. coli* host cell strains. The acetate utilization genes are induced in the transformed *E. coli* by culturing the *E. coli* in a first substrate comprising acetate, propionate, or a combination thereof until the growth reaches late log phase and thereafter culturing on a second substrate comprising glucose and optionally propionate.

The PHA copolymers produced according to the present invention can be "random" copolymers, wherein the PHA copolymer comprises PHB and PHV dispersed randomly in the polymer backbone, or as "semi-random" or blocked copolymers, wherein the PHA copolymer comprises long or short chains of one particular PHA, for example PHB, which is separated by long or short chains of other PHAs, for example randomly dispersed PHB and PHV.

The foregoing and other objects, aspects and advantages of the invention will be better understood from the following detailed description of the preferred embodiments of the invention with reference to the accompanying drawings.

BRIEF DESCRIPTION OF THE DRAWINGS

FIG. 2 is a table containing an analysis of cosmid clones for enzyme activity and PHB accumulation.

FIG. 4 is a table containing an analysis of subclones for enzyme activity and PHB production.

FIG. 11 is a table showing an analysis of PHB/PHV production in varying ratios of acetate:propionate and glucose substrates.

BEST MODE OF CARRYING OUT INVENTION

Figure 1:
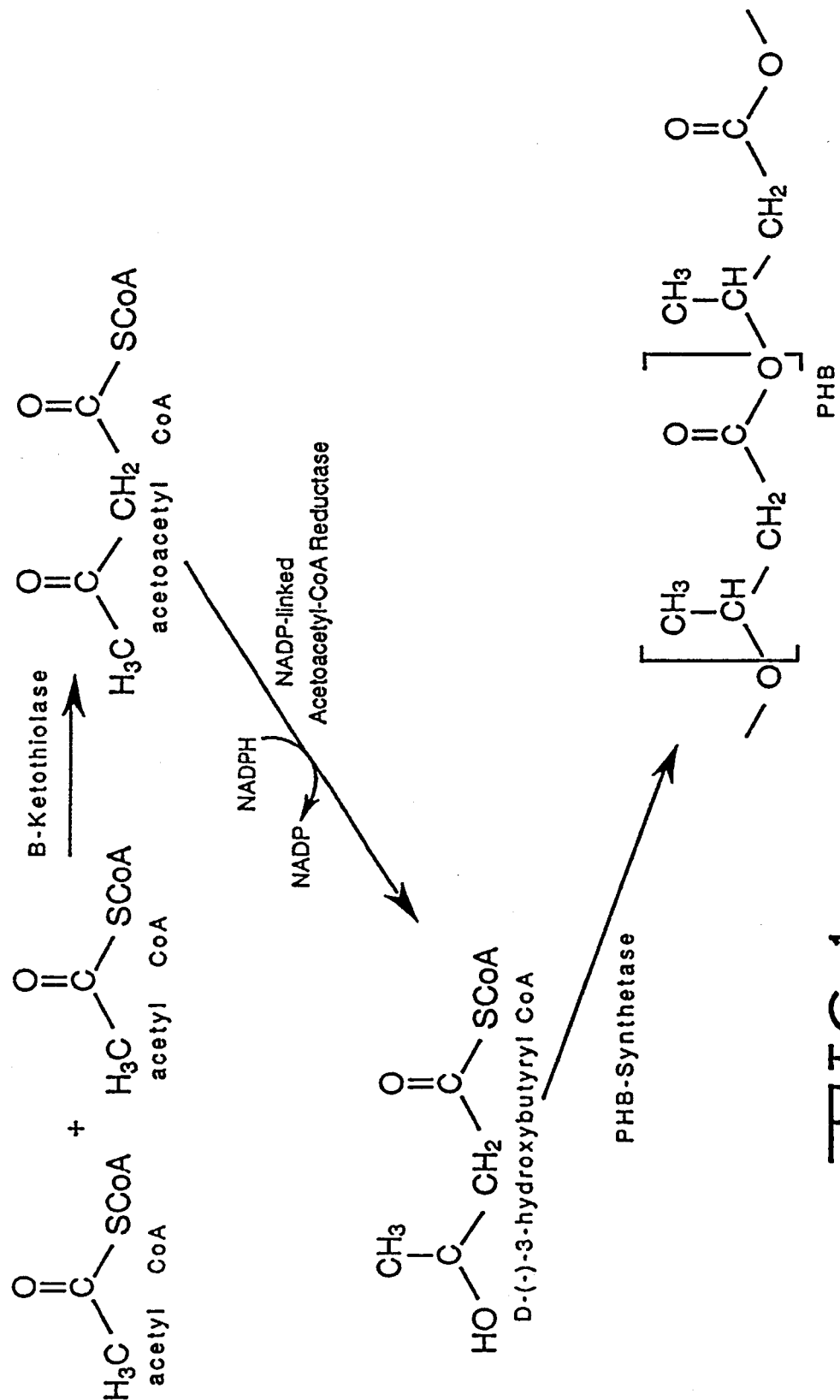
FIG. 1 is a chemical reaction sequence showing the synthesis of PHB.

Experiments have been conducted which include the cloning of the PHB biosynthetic pathway and the production of PHAs in *E. coli* to a high internal concentration. All chemicals used in the experiments were reagent grade and were obtained from the Sigma Chemical Company of Missouri or from United States Biochemicals of Ohio. *A. eutrophus* H16, *E. coli* LE392, and *E. coli* DH1 were obtained from the American Type Culture Collection (ATCC) of Maryland. *E. coli* DH5 was obtained from the Bethesda Research Laboratories. Luria Broth (LB) and antibiotics were prepared according to the methods described in Maniatas et al., *Molecular Cloning: a laboratory manual*, Cold Spring Harbor Laboratory, New York, 1982. The cosmid PVK102 was obtained in *E. coli* HB101 from the ATCC.

The methods, genes, and products of their expression and polymer synthesis are described in detail in the following non-limiting examples. Generation and Initial Screening of the *A. eutrophus* H16 Library.

A cosmid library of *A. eutrophus* H16 total DNA was constructed by inserting 20-kb to 25-kb DNA fragments in PVK102, followed by transduction of *E. coli* LE392. Total *A. eutrophus* H 16 DNA was extracted by the sarcosyl lysis method described in Pritchard et al., *Basic cloning techniques: a manual of experimental procedures*, Blackwell Scientific Publications, London, 1985. A series of partial SalI restriction endonuclease digests of the DNA was conducted in order to determine the reaction conditions that would yield the maximum percentage of DNA fragments in the 20-kb to 25 kb range. By using the parameters obtained from the calibrating reaction, a large scale digest was performed and the DNA was purified by phenol extraction and ethanol precipitation. The cosmid pVK102 was extracted according to the method of Hansen et al. J. Bacteriol., 135:227–238, 1978. The cosmid pVK102 was then purified in a cesium chloride (CsCl) gradient, digested with SalI, and purified by phenol extraction and ethanol precipitation. The partially digested genomic DNA fragments and the cosmid were mixed at an insert-to-vector molar ratio of 20:1 at a final total NA concentration of 400 ug/ml, and the mixture was subjected to ligation overnight at 14° C. Part of the ligation was packaged by using the Promega Packagene kit, available from Promega Biotec of Wiscousin, and the packaged cosmids were used to transform *E. coli* LE392. The bacteria were plated onto plates of LB plus kanamycin, and resultant clones were picked for use in the library. Approximately 1,100 clones were picked for further assay. Of these clones, nine percent were polycosmids. Clones were stored individually in LB plus 15% glycerol at −85 C.

The cosmid library was initially screened by assaying for beta-ketothiolase activity. The enzyme assay for beta-ketothiolase (thiolysis reaction) was conducted using the method of Senior et al. Biochem. J., 125:55–68, 1971, and Biochem. J., 134:225–238, 1973. Cell extracts were prepared for enzyme assay according to the following procedures: one milliliter of an overnight culture in LB was pelleted by centrifugation in a microcentrifuge for one minute; the supernatant was removed, and the pellet was resuspended in 200 ul of breaking buffer which was comprised of 20 mM potassium phosphate buffer at Ph 7.2, 5 mM magnesium chloride ($MgCl_2$), 1 mM ethylenediaminetetraacetic acid (EDTA), 1 mM dithiothreitol, and 1M glycerol; the suspension was subjected to sonication using an Artek 300 sonicator with a microprobe at the maximum setting wherein sonication consisted of four fifteen second bursts; the sonic extract was subjected to centrifugation in a microcentrifuge for five minutes; and the supernatant was transferred to a different microcentrifuge tube on ice for analysis. For assays done at later times, the cells were pelleted by centrifugation in a microcentrifuge at room temperature for one minute, the supernatant was removed and the pellets were stored at −85° C. until assay, at which time the pellets were resuspended and sonicated as described above.

In the beta-ketothiolase activity test, positive activity was measured in terms of micromoles of acetoacetyl-CoA degraded per minute per milligram of protein. Note that the reaction was assayed in the reverse direction but that one could also assay for acetoacetylCoA produced. To facilitate screening, 5 ml cultures of each clone were grown and then pooled in groups of five for assay. FIG. 2 shows that beta-ketothiolase activity was measurable in *A. eutrophus*, but not in *E. coli* LE392 lysates which had been cleared of particulate matter. Of the more than two hundred pools that were screened, six were positive for beta-ketothiolase activity. Individual clones from each pool were screened, and activity was traced to six clones which are identified in FIG. 2. The activities of the betaketothiolase-positive recombinants ranged between 50 and 15% of that found in *A. eutrophus* H16 (FIG. 2 shows the results from a single run of a series of six runs and the 50% figure was determined from the series of six runs).

Screening of the Beta-ketothiolase-positive Recombinants

The six recombinant clones which were positive for betaketothiolase activity were further screened by assaying for acetoacetyl-CoA reductase activity and by monitoring PHB accumulation. The enzyme assay for acetoacetyl-CoA reductase was conducted according to the methods covered in the Senior et al. article, supra. Acetoacetyl-CoA reductase activity was measured in terms of micromoles of NADPH oxidized per minute per milligram of protein. Protein was measured using the Bio-Rad R protein assay available from the Bio-Rad Laboratories of California. The PHB accumulation assay was done according to the method of Ward et al. Anal. Biochem., 52:607–613, 1973, except that Whatman GF/F filters were used instead of Whatman GF/A filters. PHB amounts were calculated from a standard curve by using known quantities of DL-hydroxybutyrate.

FIG. 2 shows that three recombinant clones, which harbor cosmids pAE65, pAE 175 and pAE689, respectively, were positive for acetoacetyl-CoA reductase activity and PHB production. The clone harboring PAE65 expressed acetoacetyl-CoA reductase activity to a much higher level than did *A. eutrophus* H16 but produced a very small amount of PHB. Conversely, acetoacetyl-CoA reductase activity in clones harboring pAE175 and pAE689 was extremely low when compared to that of *A. eutrophus* H16, but both clones produced PHB to approximately 50% of the concentration achieved in *A. eutrophus* H16. It is believed that the low reductase activity and high PHB production exhibited by clones harboring pAE175 and pAE689 is the norm and that pAE65 reductase activity is an artifact which results from scrambling of the DNA fragments in the cloning process. The fact that restriction digest patterns of pAE175 and pAE689 were quite similar, and the restriction digest pattern of pAE65 was quite different provides support for this belief.

Subcloning of pAE175 Fragments

Figure 3:
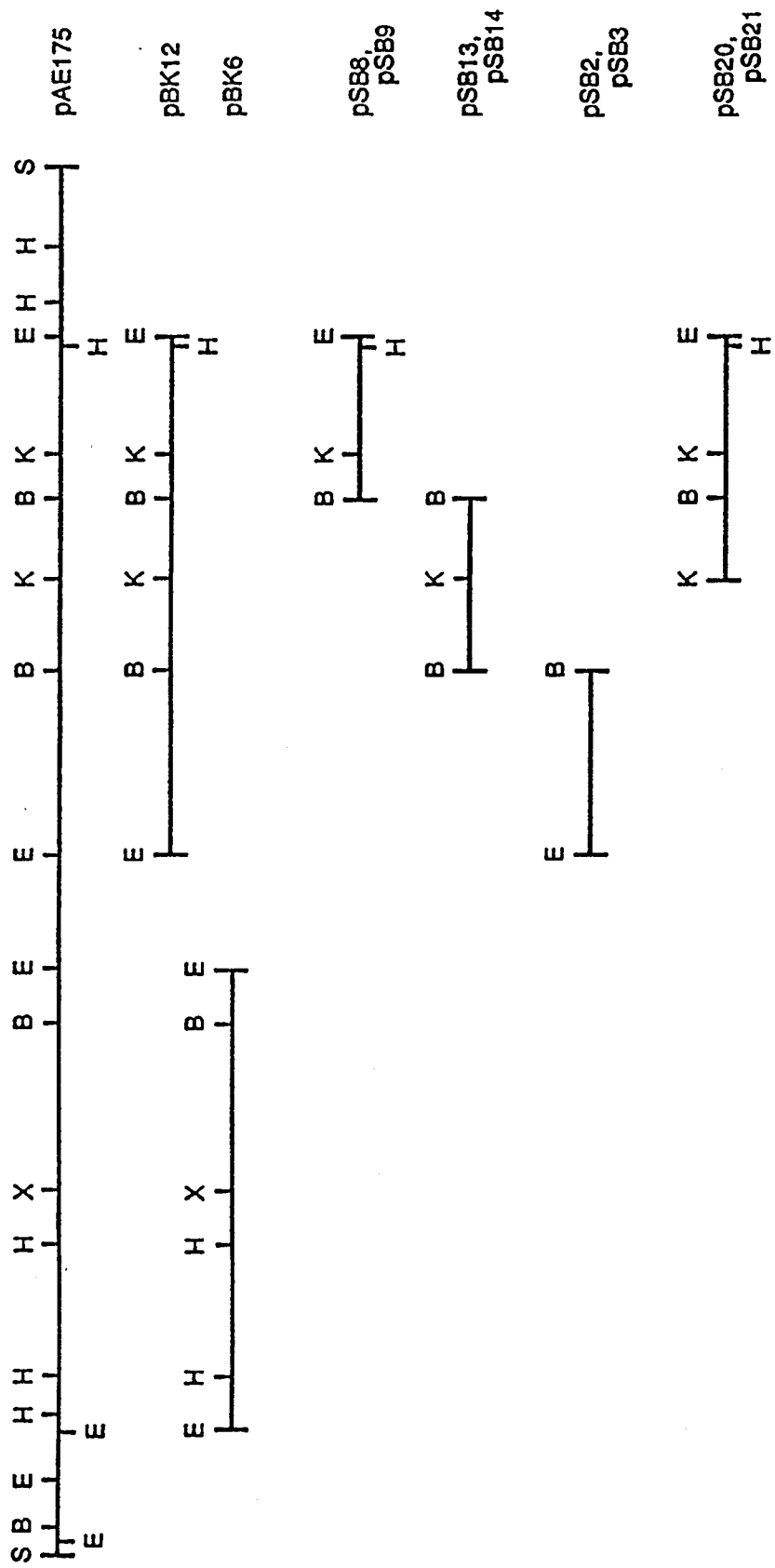
FIG. 3 is a restriction endonuclease map of the cosmid pAE175 insert showing subcloned restriction fragments; abbreviations of restriction endonucleases are as follows: B, BglII; E, EcoRI; H, BamHI; K, KpnI; X, XhoI; S, SalI.

FIG. 3 shows a restriction endonuclease map of the pAE175 cosmid DNA insert. Two central EcoRI fragments were subcloned into the plasmid pUC13, a plasmid available from Pharmacia. Subcloning of the cosmid and plasmid DNA fragments was performed according to the following procedures: recombinant cosmids were purified according to method of Hansen et al., supra; the purified recombinant cosmid was digested with the appropriate restriction endonuclease; and the fragments to be cloned were isolated in low melting temperature agarose as described in Burns, Anal. Biochem., 135:48–51, 1983. Ligation reactions contained plasmids and insert DNA at a 1:3 ratio, respectively. Restriction enzymes and T4 DNA ligase were purchased from Bethesda Research Laboratories of Maryland or from United States Biochemicals. Seakem GT agarose, available from the FMC Corp., Marine Colloids Division, of Maine, was used as the agarose.

Two clones, harboring pBK12 and pBK6 EcoRI restriction fragments, respectively, were picked and analyzed for betaketothiolase activity, acetoacetyl-CoA reductase activity, and PHB production. FIG. 4 shows an analysis of subclones for enzyme activity and PHB production where, interestingly, high betaketothiolase activity was detected in both clones. However, acetoacetyl-CoA reductase activity and PHB production was only detected in clones harboring pBK 12. The pBK 12 insert is approximately 14 kb in length. As in clones harboring pAE175 and pAE689, the acetoacetyl-CoA reductase activity in the clone harboring pBK12 was found in lower amounts than in *A. eutrophus*. PHB production in the pBK 12 harboring clone was lower than that found in the PHB producing cosmid clones.

It is known that the PHB pathway has a biosynthetic portion and a degradative portion and is made up of five enzymes. In Dawes et al., Adv. Microb. Physiol., 14: 135–266, 1973, it is pointed out that beta-ketothiolase is both the entry and exit point of the cycle. The existence of two beta-ketothiolase activities raises the possibility that the activity found on pBK12 is part of the biosynthetic portion while the activity found on pBK6 is part of the catabolic portion. To test the possibility that pBK6 contained part or all of the biodegradative pathway, the clone was assayed for two of the remaining three catabolic enzymes, D-3-hydroxybutyrate and succinyl-CoA transferase. The enzyme assays were performed according to the methods of Senior et al., supra. Neither activity was found in lysates of *E. coli* harboring pBK6, *E. coli* harboring pBK12, or *E. coli* harboring pAE175, whereas both activities were easily measured in *A. eutrophus* H16. Therefore, the betaketothiolase activity on pBK6 is unexplained; however, there is a possibility that the three remaining catabolic enzymes are simply not proximal to the beta-ketothiolase gene.

Plasmid pBK12 was further subcloned by digesting it with EcoRI and BglII. Two EcoRI-BglII fragments and one BglII fragment were obtained and each fragment was approximately 4 kb in length. Six subclones, representing each portion of the pBK12 insert in duplicate, were picked and assayed for beta-ketothiolase activity, acetoacetylCoA reductase activity, and PHB accumulation, as described above. FIG. 4 shows beta-ketothiolase activity and acetoacetyl-CoA reductase activity were detected in *E. coli* harboring plasmids pSB8 and pSB9. FIG. 3 shows the *E. coli* harboring plasmids pSB8 and pSB9 as the right most BglII-EcoRI fragment. The activities expressed in pSB8 and pSB9, shown in FIG. 4, are considerably higher than those expressed in *A. eutrophus*.

The data from analyses of pSB8 and pSB9 were interpreted to mean that the first two enzymes of the PHB biosynthetic pathway are located on the 3,500 base BglII-EcoRI fragment, but that the third enzyme, PHB synthetase, was either cleaved by BglII or is positioned to the left of the BglII site. To obtain the whole pathway on a sequence small enough to use in DNA sequence studies, a 5.5 kb KpnI-EcoRI fragment was cloned into pUC18, a plasmid obtained from Bethesda Research Laboratories of Maryland. Two clones harboring pSB20 and pSB21 were tested and both clones exhibited betaketothiolase activity, acetoacetyl-CoA reductase activity and PHB production. FIG. 4 shows the subclones pSB20 and pSB21 accumulated nearly as much or more PHB as *A. eutrophus* H16. FIG. 3 shows a restriction endonuclease map of the pSB20 and pSB21 fragments relative to the pAE175 cosmid insert.

Comparison of *A. eutrophus* H16 DNA with Cloned DNA

Figure 5:
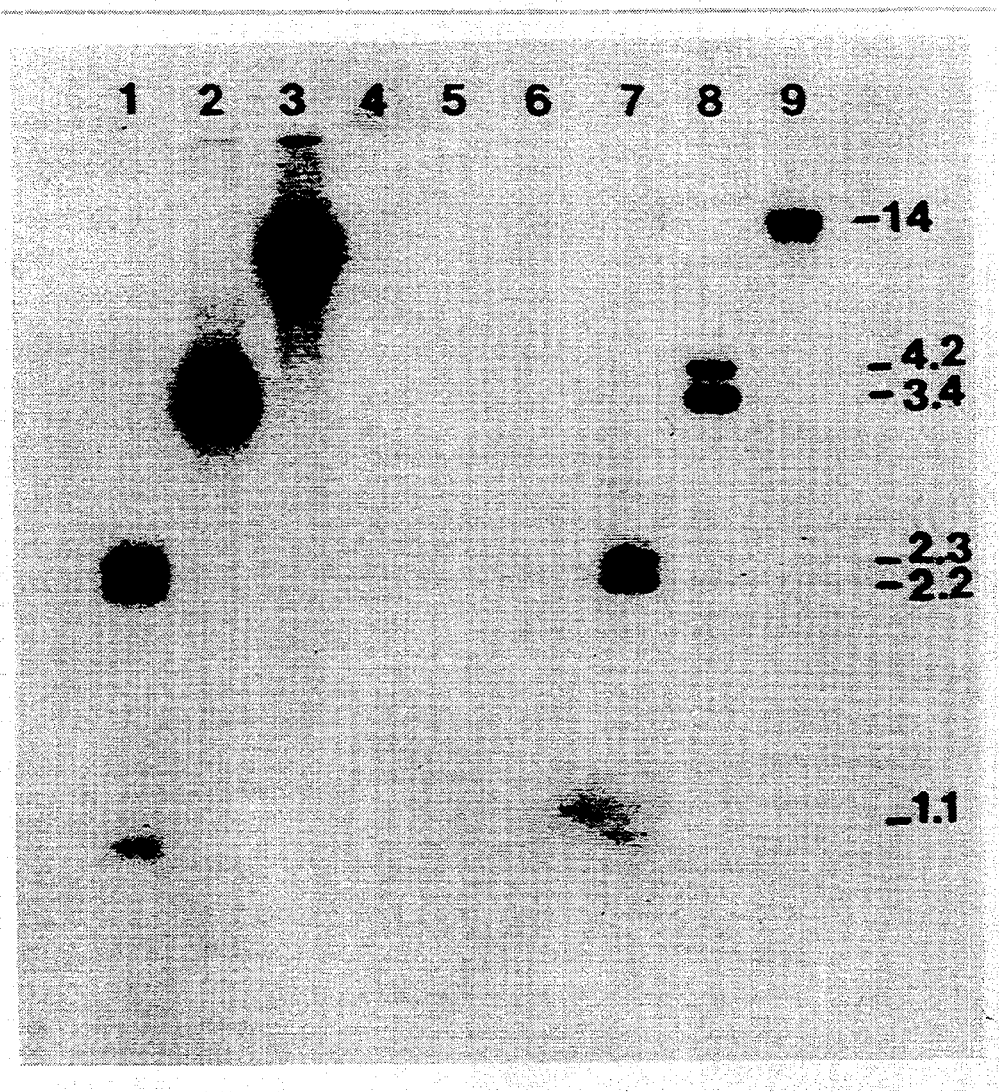
FIG. 5 is a Southern blot analysis of DNA from *E. coli* harboring PAE175 (lanes 1 to 3), *E. coli* LE392 lanes 4 to 6) and *A. eutrophus* H15 genomic DNA (lanes 7–9); lanes 1, 4 and 7, EcoRI; lanes 2, 5 and 8, EcoRI-BglII; lanes 3, 6 and 9, SalI.

Because the manner in which the PHB pathway was cloned left open the possibility that the cloned fragment was a product of scrambling, Southern blot analysis was performed to demonstrate that the PHB biosynthetic pathway in *A. eutrophus* H16 has the same restriction pattern as that of the cloned PHB DNA. Southern blot analysis was performed by the method of Maniatis et al., supra. The probe was made radioactive by using a random primer extension kit obtained from DuPont, NEN Research Products, of Massachusetts. Digested pAE175 was compared to digests of DNA extracted from *A. eutrophus* H16 and *E. coli* LE392. Restriction endonucleases used were EcoRI, EcoRI-BglII, and SalI, respectively. A gel purified 5.2 kb PHB fragment was labeled and used as a probe. FIG. 5 reveals that the PHB biosynthetic pathway is located on a 14 kb EcoRI fragment in *A. eutrophus* H16 (shown in lane 7) and in pAE175 (shown in lane 1). No hybridization could be detected to any DNA fragments to *E. coli* LE392 Ganes 4 through 6). Further digests of pAE175 and *A. eutrophus* genomic DNA manifested the same restriction patterns, indicating that the cloned PHB biosynthetic pathway was the same as that found in *A. eutrophus* H16.

PHB in E. coli

Figure 6A:
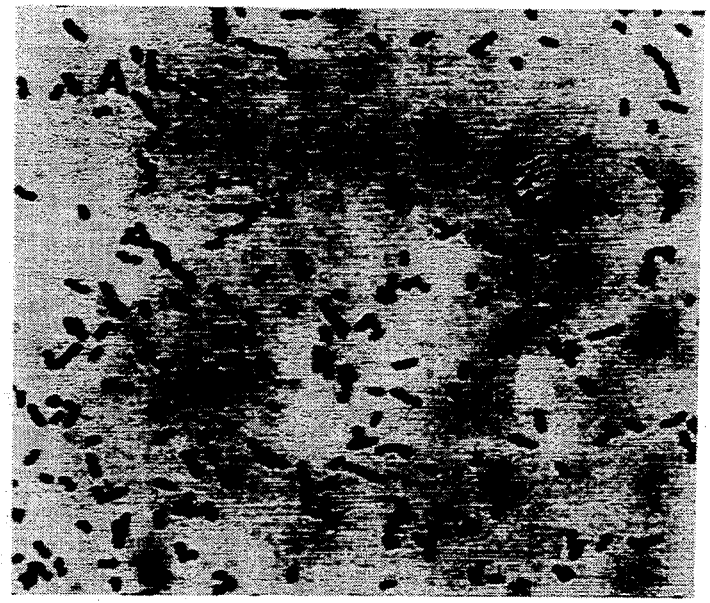
FIGS. 6a and 6b are photomicrographs of *A. eutrophus* H16 and *E. coli* harboring PSB20, respectively, showing intracellular PHB granules (arrows); magnification, ca. x3.000.
Figure 6B:
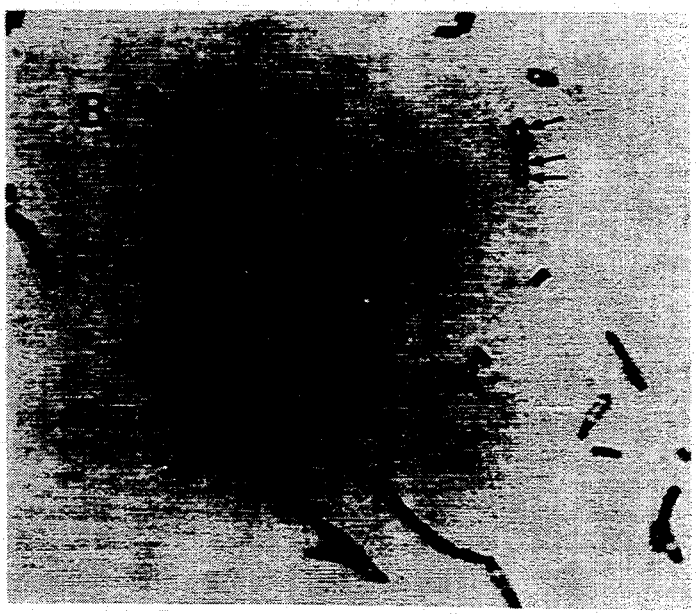

FIGS. 6a and 6b show that PHB is produced in granules in both *A. eutrophus* H16 and *E. coli* harboring the pSB20 plasmid insert. Twenty four hour cultures of *A. eutrophus* H16 and *E. coli* harboring pSB20 were stained for fifteen seconds with crystal violet. The crystal violet is absorbed by the cells, but PHB granules are refractile to the stain. The cultures were examined under an oil immersion lens. FIG. 6a shows PHB granules in *A. eutrophus* are evident as fuzzy, non-staining areas between stained regions of the bacterium. FIG. 6b shows PHB granules in *E. coli* much more distinctly. Granule formation in *E. coli* appears to differ from that in *A. eutrophus* H16 in that the granules in *E. coli* were more numerous and were often larger in diameter than the cell. PHB granules in *A. eutrophus* H16 did not usually distend the cell membrane.

Figure 7:
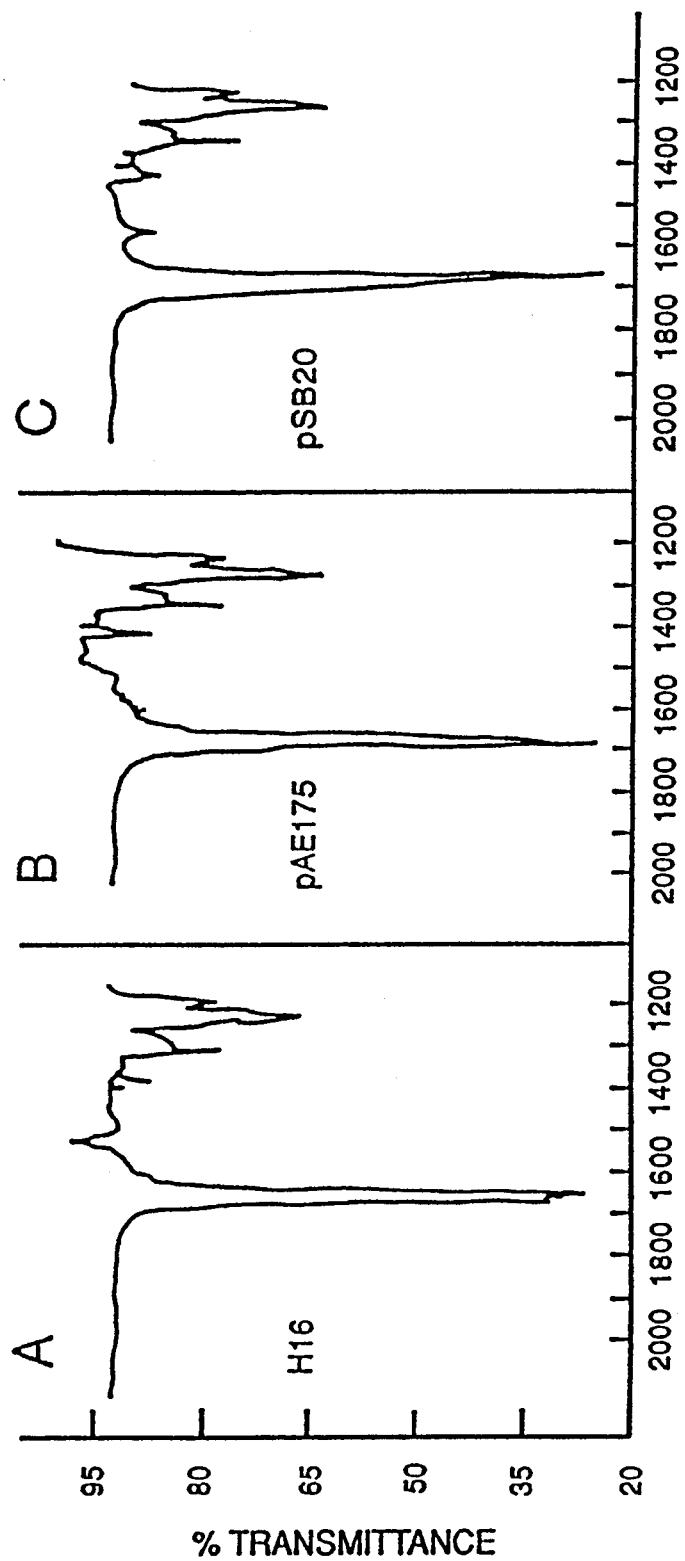
FIG. 7 is a graph showing infrared (IR) spectra of PHB extracted from *A. eutrophus* (A), *E. coli* harboring PAE175 (B), and *E. coli* harboring PSB20 (C).

FIG. 7 shows IR spectra of PHB which was extracted from *A. eutrophus* (A), *E. coli* harboring pAE175 (B), and *E. coli* harboring pSB20 (C). The infrared (IR) spectra of various PHB samples was obtained utilizing the technique described in Wakisaka, Appln. Environ. Microbiol., 43:1473–1480, 1982. The results demonstrate that the PHB produced in its native state (i.e., in *A. eutrophus* H16) and PHB produced in the transformed *E. coli* (i.e., *E. coli* harboring pAE175 and *E. coli* harboring pSB20) have virtually identical IR spectra. In addition, the PHB spectra shown in FIG. 7 are very similar to those from other organisms as indicated in Fernandex-Casillo et al., Appl. Environ. Microbiol., 51:214–216, 1986, and in Senior et al., supra.

Production of PHB

Experimental results showed that *E. coli* harboring both pAE175 and pAE689 cosmid clones produced PHB to approximately 50% of the level achieved in *A. eutrophus* H 16 while expressing reductase levels that were less than 2% of reductase levels in *A. eutrophus* H16. Substantial levels of intracellular PHB were accumulated in *E. coli*. These levels approached 90% of the bacterial cell dry weight in some subclones, and PHB was observable as large intracellular bodies. The high levels of expression obtained implies either a high degree of transcriptional versatility or a high degree of transcriptional homology.

PHB was grown in *E. coli* harboring the PHB biosynthetic genes under conducive conditions, i.e., a flask of LB is innoculated with the *E. coli* harboring the PHB biosynthetic pathway and the *E. coli* are grown in the presence of 1% glucose (where glucose acts as the carbon source for PHB production).

A strain of *E. coli* harboring the PHB biosynthetic pathway which was produced according to the techniques described above has been deposited with the American Type Culture Collection of 12301 Parklawn Drive, Rockville, Md. on Jun. 5, 1989 and bears deposit number: 68006. The strain (pGEM-PHB) is like that of pSB20 where the PHB biosynthetic pathway was isolated on a DNA fragment approximately 5.5 kb in length. The advantage of the smaller vector over the larger cosmid clone pAE175 is the ability to produce more copies. Access to the microorganism shall be made available to the public.

p4A Subclone

A strain of *E. coli*, i.e., *E. coil HMS* 174, was transformed by a vector containing the p4A plasmid with the PHB biosynthetic pathway and approximately four hundred extra bases on both the upstream and downstream sides of the pathway. The HMS174 strain of *E. coli* was chosen because it contains a lactose utilization system and is recombination deficient so that a plasmid containing lactose genetic regions will not recombine and make the construct unstable.

Figure 9:
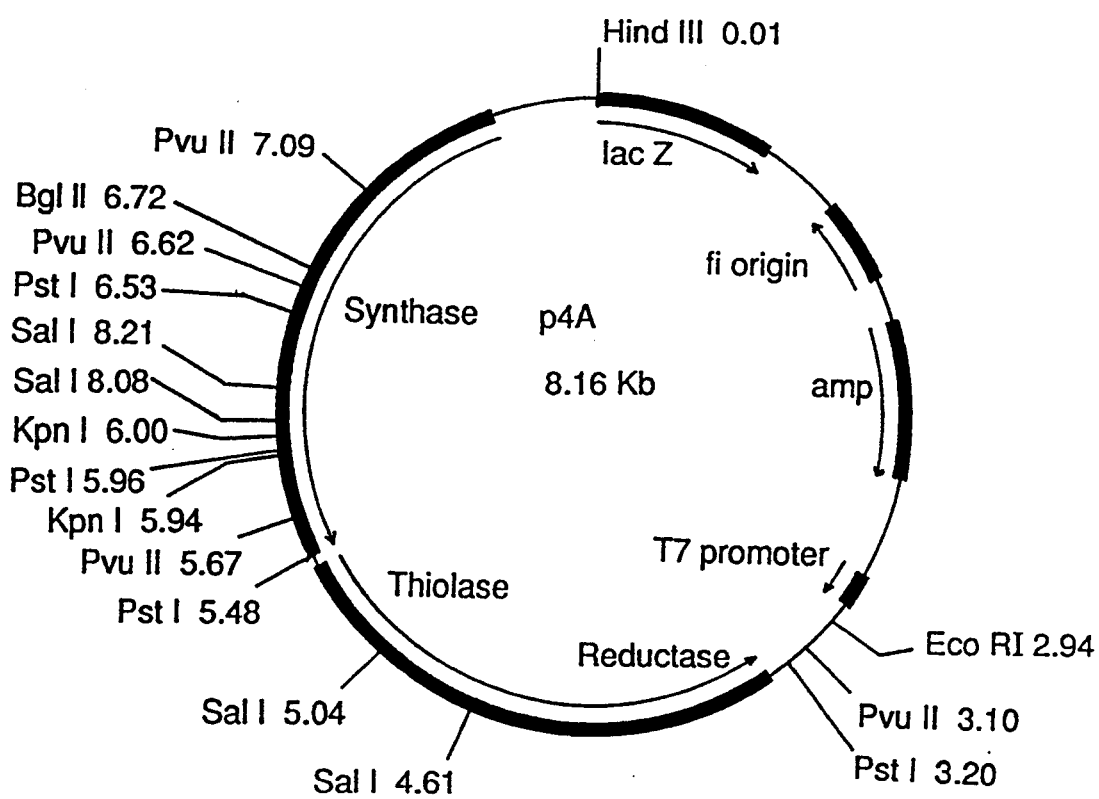
FIG. 9 is a diagram of the plasmid p4A.
Figure 10:
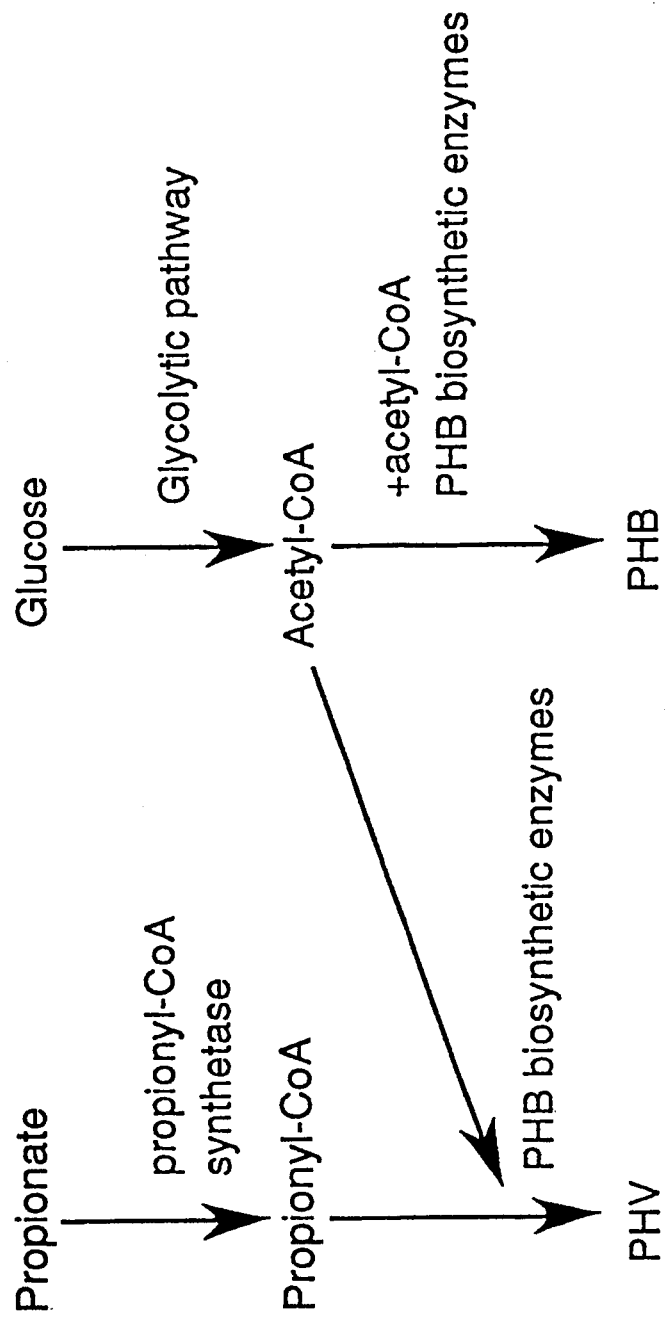
FIG. 10 is a schematic diagram of a pathway of PHB-coV production.

The *E. coli* strain HMS174 containing the plasmid p4A accumulates a greater percentage of PHB in a shorter period of time than other *E. coli* clones containing different plasmid constructs. The *E. coli* strain HMS174 is available from the Yale *E. coli* Stock Center, Barbara Bachman, curator. Clone (plasmid) p4A which contains the DNA for the poly-beta-hydroxybutyrate biosynthetic pathway was deposited in an *E. coli* HMS174 host in the permanent collection of the American Type Culture Collection, 12301 Parklawn Drive, Rockville, Md., on May 23, 1990. The culture was assigned the accession number ATCC: 68329 by the repository. Recombinant plasmid p4A can be isolated from its *E. coli* HMS174 host by well known procedures, e.g., using alkaline lysis procedures, and the like. The p4A clone is shown in FIG. 9 and is described in the copending application Ser. Nos. 07/528,549, filed May 25, 1990 and 07/705,806, filed May 24, 1991, and published in Janes et al., E. A. Dawes (ed.) Novel Biodegradable Microbiol Polymers 175–190, 1990, Kluwer Academic Publishers (printed in The Netherlands), all of which are expressly incorporated herein by reference.

The p4A plasmid exists in the cell at an abnormally high copy number (50–200 per cell) thereby increasing the gene dosage of the PHB biosynthetic genes resulting in extremely high PHB production (as high as 95% of the cell weight). Thus, p4A is a "multicopy plasmid". The term "multicopy plasmid" is used in the sense of the ordinary definition and means a plasmid which exists in a plural number in a host cell.

The p4A construct has been placed in several different host strains, including *E. coli* strains, for example, DH1, DH5, BW313, HMS174, and CJ236. In all instances PHB was made to levels reaching 70–95% PHB wt/cell wt. It is to be noted that various other bacterial strains including, for example, Salmonella or other euteric organisms can also be used as the host strains.

The plasmid p4A is superior to other plasmids based on its copy number, because in alkaline minipreps the plasmid yield from p4A is about twice as much as other PHB-plasmids. Gene dosage effect may be responsible for high levels of PHB production in *E. coli*. To test this hypothesis, the PHB pathway was cloned into plasmid pOU71 obtained from Dr. Soren Molin (Larsen et al., Gene 28:45, 1984). This plasmid is maintained as a single copy when grown at 30° C. In experiments where the plasmid was maintained as a single copy, PHB production was 1/40th of that found in p4A in *E. coli* DH5alpha. If the PHB genes are found in single copies in *A. eutrophus*, this indicates that the genes are not well-expressed in *E. coli*, but overcome this deficit by having a large number of genes. This is supported by reports that, in general, *A. eutrophus* genes are poorly expressed in *E. coli* (Andersen et al., J. Bact. 159:97, 1984).

PHA in E. coli

Figure 8:
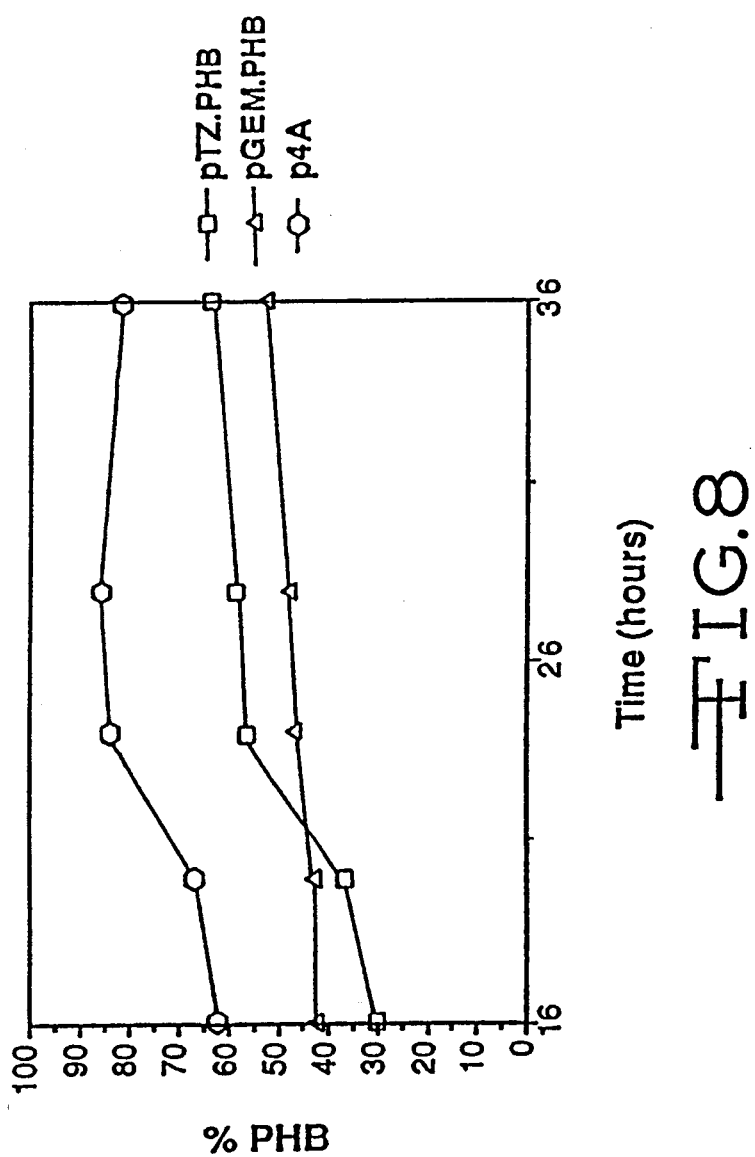
FIG. 8 is a line graph showing PHB accumulation versus time for a variety of clones containing different plasmid constructs.

Acetyl-CoA synthetase is able to utilize propionate as a substrate and change it to propionyl-CoA. Propionyl-CoA is then incorporated directly into PHB-co-V starting with the PHB biosynthetic enzyme beta-ketothiolase. The first enzyme of the PHB pathway, beta-ketothiolase, has a substrate specificity that allows it to act on propionyl-CoA as well as acetyl-CoA (Haywood et al., FEMS Microbiol. Letters 52:91, 1988). It has been proposed that acetyl-CoA synthetase accepts propionate as well as it's normal substrate, acetate (Campagnari et al., J. Biol. Chem. 238:1628, 1963; Hele, J. Biol. Chem. 206:671, 1952). Thus, the pathway of PHB-co-V production, as shown in FIG. 8, is believed to be as follows: propionyl-CoA and acetyl-CoA are condensed to acetopropionyl-CoA, which is then reduced to beta-hydroxyvaleryl CoA, which is subsequently polymerized into the PHB/PHV copolymer.

The enzymes needed for PHB-co-V production are not normally to be found in most host strains, including E. coli. However, acetylCoA synthetase is an inducible enzyme of the acetate utilization system in many host strains, including for example, Escherichia and Salmonella. According to the method of the present invention PHA production in the host is accomplished by inducing acetate utilization genes in a host and thereafter producing the PHAs by allowing the host cells containing the acetate utilization genes to grow.

In one embodiment of the invention, a vector containing the DNA sequence coding for the poly-beta-hydroxybutyrate biosynthetic pathway is introduced into the host cell. The enzymes of acetate utilization are induced by growing the host cells on a first substrate. The first substrate comprises at least one of the following: acetate, propionate, or combination of acetate and propionate, or other 3carbon substrate. In a preferred embodiment the host cells are allowed to grow in the first substrate until the culture reaches late log phase. Thereafter, the host cells are cultured on a second substrate comprising a carbon source such as glucose, fructose, sucrose, lactose, maltose and the like. Alternatively, the host cell can be cultured in the first substrate prior to introducing the vector. The enzymes of acetate utilization, now present in the host cells, act on the propionate and incorporate the propionate into the PHA copolymers being produced by the host cells. The ratios between the various PHAs can be varied by altering the ratio between the first substrates. For example, acetate:propionate ratios can vary between 20-40:10-25 to produce concentration of PHV as high as about 50%, by weight, of the PHAs produced.

In another embodiment, the host can be a mutant in which the genes for acetate utilization are expressed constitutively. That is, they are present at all times. The p4A plasmid described above was cloned into E. coli cells which produced acetyl-CoA synthetase. The transformed E. coli cells were then grown on a substrate which comprises propionate and a carbon source. It is noted that various other carbon sources such as sucrose, fructose, lactose, maltose and the like are also useful as carbon sources in the present invention. These clones are able to incorporate propionate to form a copolymer comprising PHB and PHV.

The acetyl-CoA synthetase must be present in order to obtain PHV synthesis. Thus, in another embodiment, the acetyl-CoA synthetase gene can be cloned onto a plasmid and expression of the acetyl-CoA synthetase gene can be obtained from the plasmid. These clones can be used in a number of ways to regulate PHV synthesis; for example, PHV synthesis only occurs when the cloned acetyl-CoA synthetase gene is turned on.

The PHB/V currently produced is a random copolymer in that the valerate and butyrate are dispersed randomly in the polymer backbone. However, by controlling (by activating or suppressing) the acetate utilization gene it is now possible to generate "blocked" or semi-random copolymers. By alternately turning on and turning off the acetate utilization genes for a period of time (using, for example, chemical or heat induction) semi-random polymers are generated. The semi-random polymers comprise chains of butyrate molecules interspersed with chains of randomly dispersed molecules of butyrate and valerate. In addition, as described above, by controlling or varying the substrate, the composition of the PHAs generated are also varied.

The clones used in the present invention, when grown on the various substrates produce a copolymer of PHB/V to levels reaching 80–85% of the total cell weight. By varying the amount of propionate, it is possible to alter the ratio of PHB to PHV production by the host cell. PHV production up to and including about 50% by weight of the total cells weight, can be achieved using the present invention.

The following examples present non-limiting examples of the method of the present invention.

INDUSTRIAL APPLICABILITY

The enzymes of acetate utilization were induced in E. coli. The three E. coli strains used were obtained from the E. coli Genetic Repository at Yale University from Barbara Bachman. Two of the strains, E. coli 5219 and E. coli 5221 are mutants in acetate utilization, whereas the third strain, E. coli 5218 expresses the acetate utilization genes constitutively.

Example 1

Acetate utilization genes were induced in various E. coli strains, and then grown on acetate/propionate substrates, with and without glucose, E. coli 5218, 5219 and 5221 were grown in Luria broth overnight. The cells were pelleted and resuspended in M9 minimal media containing 40 mM acetate:10 mM propionate. 45 ml of same medium was added to resuspension in 250 ml baffled flask and grown to O.D.(600) of 0.7. The culture was electroporated with p4A wherein electrical pulses of high field strength are used to reversibly permeabilize the cell membranes to facilitate the uptake of the p4A plasmid. Immediately after electroporation the same medium was innoculated with ampicillin at 200 ug/ml. Thereafter this medium was put into two flasks and 0.4% glucose was added to one of these flasks. The result was two cultures: one with glucose, and one without, both with acetate and propionate. The cultures were allowed to grow. It was noted that the E. coli 5221 (PHA) was fastest. After 4 days' growth the optical density O.D.(600) was measured:

|  | Ac/Prop | Ac/Prop/Gluc |
|---|---|---|
| E. coli 5218(PHA) | 0.1 | 4.78 |
| E. coli 5219(PHA) | 1.4 | 3.34 |
| E. coli 5221(PHA) | 1 | 4.74 |

GC analysis (in integration units) was measured:

|  | Ac/Prop | |
|---|---|---|
|  | PHB | PHV |
| E. Coli 5218(PHA) | 21,000 | 0 |
| E. Coli 5219(PHA) | 22,000 | 0 |
| E. Coli 5221(PHA) | 37,000 | 0 |

-continued

| | Ac/Prop/Gluc | | | |
|---|---|---|---|---|
| | PHB | % | PHV | % |
| E. coli 5218(PHA) | 544,000 | 93 | 43,000 | 7 |
| E. coli 5219(PHA) | 27,000 | | 0 | |
| E. coli 5221(PHA) | 804,000 | 96 | 34,000 | 4 |

The above data show that at least about 5%, by weight based on total PHB/V production, of PHV can be made by inducing acetate utilization genes in a bacterial host.

Example 2

The effect of alterations of the acetate:propionate ratios on PHB/PHV production were evaluated. A culture of E. coli 5218(PHA) was grown overnight in Minimal Media +10 mM acetate +50 mM propionate. E. coli 5218(PHA) was innoculated into two cultures as follows: Culture A contained 40 mM acetate/10 mM propionate in M9, and Culture B contained 20 mM acetate/25 mM propionate in M9. Both A and B cultures were allowed to grow to late log phase and then glucose to 0.4% was added to each culture. After 48 hours, GC analysis (integration units) was performed:

Culture A PHB=267,000 (76%) PHV=85,000 (24%)

Culture B PHB=160,000 (51%) PHV=154,000 (49%)

The above data show that by altering the acetate/propionate ratios, the PHV concentration can be altered and that nearly 50% PHV was obtained in culture B.

Example 3

Further, alterations of acetate:propionate ratio were made in order to evaluate alterations in the ratio of PHB:PHV production. This example is similar to Example 2 but was conducted using E. coli 5218(PHA), 5219(PHA), 5221(PHA).

40 mM At/10 mM Prop

On day 1 of the cultures GS (integration units) analysis was measured:

| | PHB | % | PHV | % |
|---|---|---|---|---|
| E. coli 5218(PHA) | 259,000 | 76 | 80,000 | 24 |
| E. coli 5219(PHA) | 35,000 | 73 | 14,000 | 27 |
| E. coli 5221(PHA) | 54,000 | 100 | 0 | 0 |

On day 2 of the cultures GS (integration units) analysis was measured:

| | PHB | % | PHV | % |
|---|---|---|---|---|
| E. coli 5218(PHA) | 303,000 | 77 | 88,000 | 23 |
| E. coli 5219(PHA) | 43,000 | 69 | 19,000 | 31 |
| E. coli 5221(PHA) | 55,000 | 100 | 0 | 0 |

On day 3 of the cultures GS (integration units) analysis was measured:

| | PHB | % | PHV | 96 |
|---|---|---|---|---|
| E. coli 5218(PHA) | 371,000 | 76 | 114,000 | 24 |
| E. coli 5219(PHA) | 47,000 | 72 | 18,000 | 26 |
| E. coli 5221(PHA) | 54,000 | 100 | 0 | 0 |

20 mM Ac/25 mM Prop

On day 1 of the cultures GS (integration units) analysis was measured:

| | PHB | % | PHV | % |
|---|---|---|---|---|
| E. coli 5218(PHA) | 143,000 | 52 | 134,000 | 48 |
| E. coli 5219(PHA) | 30,000 | 61 | 19,000 | 39 |
| E. coli 5221(PHA) | 23,000 | 77 | 7,000 | 23 |

On day 2 of the cultures GS (integration units) analysis was measured:

| | PHB | % | PHV | % |
|---|---|---|---|---|
| E. coli 5218(PHA) | 166,000 | 53 | 145,000 | 47 |
| E. coli 5219(PHA) | 36,000 | 61 | 23,000 | 39 |
| E. coli 5221(PHA) | 25,000 | 78 | 7,000 | 22 |

On day 3 of the cultures GS(integration units) analysis was measured:

| | PHB | % | PHV | % |
|---|---|---|---|---|
| E. coli 5218(PHA) | 174,000 | 53 | 157,000 | 47 |
| E. coli 5219(PHA) | 37,000 | 60 | 24,000 | 40 |
| E. coli 5221(PHA) | 25,000 | 69 | 11,000 | 31 |

In all three experiments described above, an increase in propionate in the culture medium caused an increase in the production of polyhydroxyvalerate. The percentage of PHV production ranged from about 0-30%, based on total percentage of PHB/V produced for 40 mM At/10 mM Prop to about 20-50% for 20 mM Ac/25 mM Prop.

Example 4

The PHV synthesis can be induced in any host that contains the acetate utilization pathway. E. coli HMS174/(p4A) was grown on a minimal whey plate and then transferred into M9+25 mM propionate. The culture was grown very slowly to reach O.D. (600) of 0.3. At this time, glucose to 0.8% was added. The culture was grown overnight and a GC analysis was performed on culture. GC showed 37,000 integration units for PHB, and 25,000 integration units for PHV. The percentage of PHB to PHV produced was about 60:40. Thus, PHV synthesis was induced in the HS174/(p4A).

Example 5

The strains were inoculated from LBg broth into various media to determine whether acetate induction is necessary in order to produce both PHB and PHV, as seen in FIG. 11. Acetate induction is not needed for E. coli 5218 (which is constituitive for acetate utilization). Copolymer production in such constituitive strain is achieved by culturing the strain in a substrate having the preferred propionate:glucose ratios. However, acetate induction appears to be necessary in non-constituitive strains. It was determined that propionate in the substrate is necessary for valerate production.

Example 6

PHB/V was isolated and evaluated for its physical properties. Cells were grown as above in Example 5 for E. coli 5218(PHA). The resulting material was isolated by Soxhlet extraction. The analysis of the final material was 84% PHB and 16% PHV. A solution cast film exhibited transparency and flexibility properties favorably comparable to a commercially available film made from a PHB-CoV copolymer obtained from *A. eutrophus*.

Example 7

Various copolymers produced according to the above examples were examined to determine whether valerate was present in the copolymer. The addition of valerate to the polymer causes a decrease in melting temperature of the polymer as measured by differential scanning calorimetry. A series of tests were run on polymers from different sources.

| | |
|---|---|
| PHB* | Tm = 173.4° C. |
| PHB* | Tm = 173.15° C. |
| E. coli (PHB) | Tm = 174.6° C. |
| PHB/V (70/30)* | Tm = 116° C. |
| E. coli PHB/V (84/16) | Tm = 158° C. |

*commercially obtained from separate sources

The *E. coli* PHB/V copolymer has decreased melting temperature which corroborates the other data that the copolymer is PHB/V.

Example 8

Two GC/MS were performed on the purified PHB/V obtained in the Example 6 above. The chromatograms shown in FIG. 13 indicate that the peaks identified are butyrate and valerate.

Example 9

Copolymers of PHB and PHV were produced from a host cell which was made recombinant stable using the recA protein. *E. coli* 5218 having the p4A plasmid was made recA using a P1 lysate that had been passed through a recA strain in order to allow for plasmid stability. The culture was grown in LB+glucose, then reinoculated into two cultures: Culture A was minimal media+glucose, and Culture B was minimal media+whey. When each culture reached O.D. of 0.8, propionate was added to 20 mM of each culture. The cultures were grown overnight. A GC analysis was performed.

Culture A PHB=69,000 (79%) PHV=17,500 (21%)
Culture B PHB=63,000 (89%) PHV=10,000 (11%)

The *E. coli* 5218(PHA) recA still produces PHB/V. Prior acetate induction is not needed for this particular clone. A strain of this clone which was produced according to the techniques described above has been deposited with the American Type Culture Collection of 12301 Parklawn Drive, Rockville, Md., on Aug. 29, 1991 and bears deposit number: ATCC 68681. Access to the microorganism shall be made available to the public.

Example 10

The *E. coli* 5218(PHA) recA strain was evaluated to determine whether alteration in the amount of propionate in the substrate alters the ratio PHB/V production. The *E. coli* 5218(PHA) recA strain was grown overnight in LB+1% glucose. This culture was then used to inoculate 8 cultures which had M9+1% glucose. These minimal cultures were grown to O.D. of 0.8, then propionate at varying concentrations was added. Cultures were grown and samples taken for GC at 24 and 48 hours.

At 24 hours:

| Culture | O.D. | PHB | % | PHV | % |
|---|---|---|---|---|---|
| 0 mM Prop | 10.9 | 559,000 | 100 | 0 | 0 |
| 10 mM Prop | 10.7 | 470,000 | 65 | 247,000 | 35 |
| 20 mM Prop | 10.9 | 455,000 | 63 | 269,000 | 37 |
| 30 mM Prop | 12.1 | 432,000 | 61 | 270,000 | 39 |
| 40 mM Prop | 11.2 | 478,000 | 59 | 325,000 | 41 |
| 50 mM Prop | 10.9 | 487,000 | 63 | 288,000 | 37 |
| 100 mM Prop | 10.1 | 365,000 | 51 | 352,000 | 49 |
| 200 mM Prop | 1.8 | 0 | 0 | 0 | 0 |

At 48 hours:

| Culture | O.D. | PHB | % | PHV | % |
|---|---|---|---|---|---|
| O mM Prop | 10.9 | 540,000 | 100 | 0 | 0 |
| 10 mM Prop | 10.7 | 513,000 | 69 | 227,000 | 31 |
| 20 mM Prop | 11 | 441,000 | 63 | 256,000 | 37 |
| 30 mM Prop | 11.1 | 533,000 | 65 | 290,000 | 35 |
| 40 mM Prop | 10.9 | 535,000 | 63 | 310,000 | 37 |
| 50 mM Prop | 10.7 | 518,000 | 66 | 267,000 | 34 |
| 100 mM Prop | 10.1 | 299,000 | 50 | 298,000 | 50 |
| 200 mM Prop | 1.1 | 0 | 0 | 0 | 0 |

In the examples above it is seen that an increase in the concentration of propionate in the substrate caused an increase in the production of PHV, which ranged from about 30–50%, based on the total percent of PHB/V produced.

Example 11

*E. coli* 5218(p4A)recA was innoculated into M9 media containing 25 mM acetate as carbon source. This was grown overnight (as a 50-ml culture in 250 ml shake flask) at 37° C. with shaking at 260 rpm. Two ml of the overnight culture was added to each of 6 flash of M9 medium containing 20 mM acetate as carbon source. The bacterial cultures were grown at 37° C., 260 rpm shaking until the cultures reached an optical density (at 600 nm) of approximately 0.8 (about 8 hours). At this time, propionate was added to each flask such that the flasks had propionate levels of 2.5 mM, 5 mM, 7.5 mM, 10 mM, 20 mM, and 40 mM, respectively. The cultures were allowed to grow for another hour, and then glucose was added to a final concentration of 1%. The cultures were allowed to grow for another 20 hours as above and then were harvested and analyzed by gas chromatography for valerate %.

| Culture | % PHB | % PHV |
|---|---|---|
| 2.5 mM Prop | 93 | 7 |
| 5.0 mM Prop | 91 | 9 |
| 7.5 mM Prop | 85 | 15 |
| 10 mM Prop | 90 | 10 |
| 20 mM Prop | 82 | 18 |
| 40 mM Prop | 76 | 24 |

Figure 12:
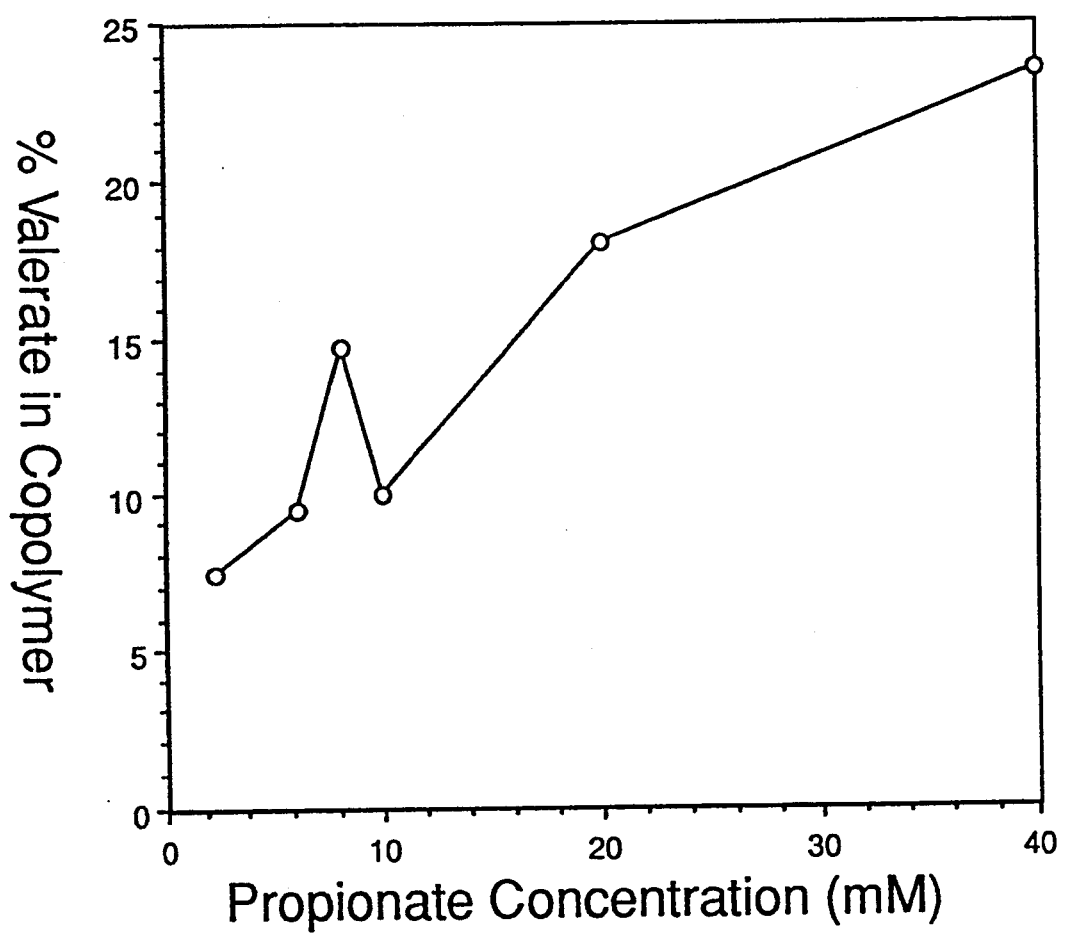
FIG. 12 is a graph showing valerate incorporation as a function of propionate concentration.
Figure 13A:
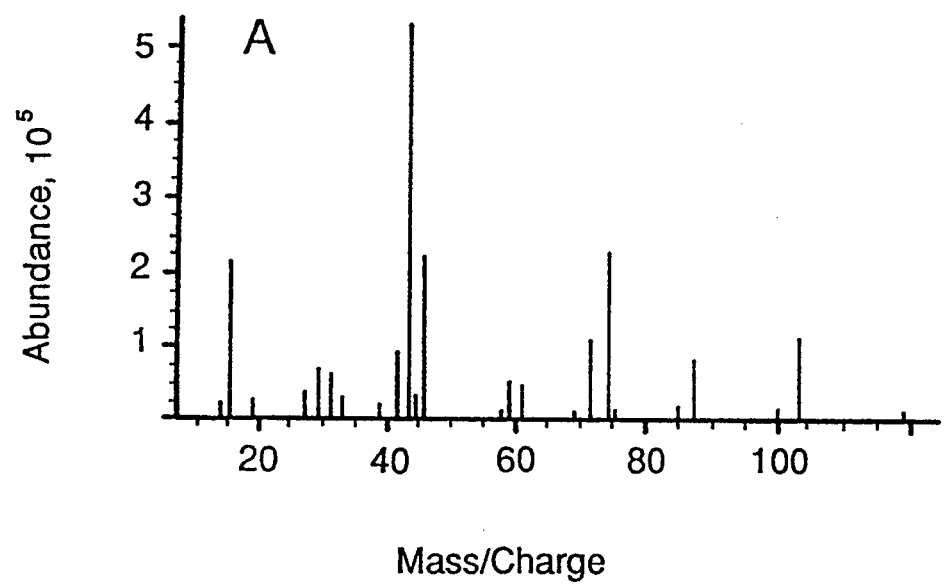
FIGS. 13A–13D are a series of graphs showing the gas chromatograph/mass spectrometer on purified PHB and PHV: graph A is a standard GC/MS of hydroxybutyrate; graph B is a standard GL/MS of hydroxyvalerate; graph C is the GC/MS of the PHB produced in Example 6; and, graph is the GC/MS of the PHV produced in Example 6.
Figure 13B:
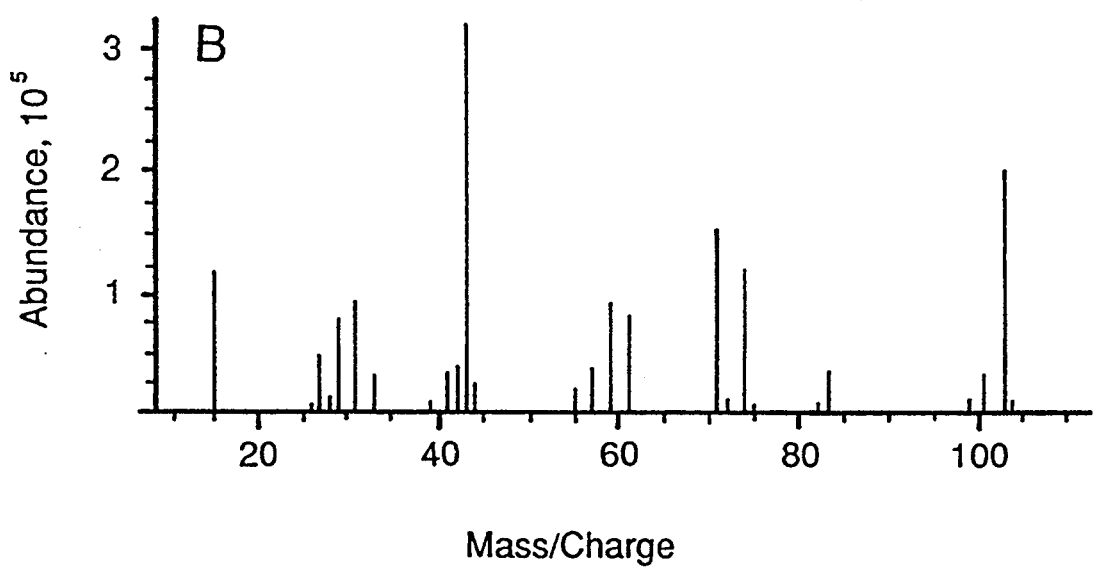
Figure 13C:
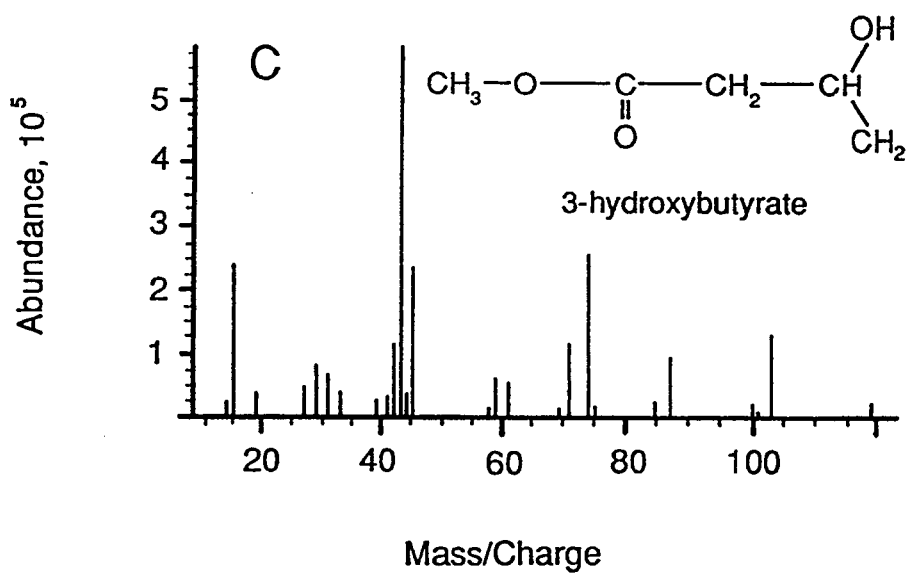
Figure 13D:
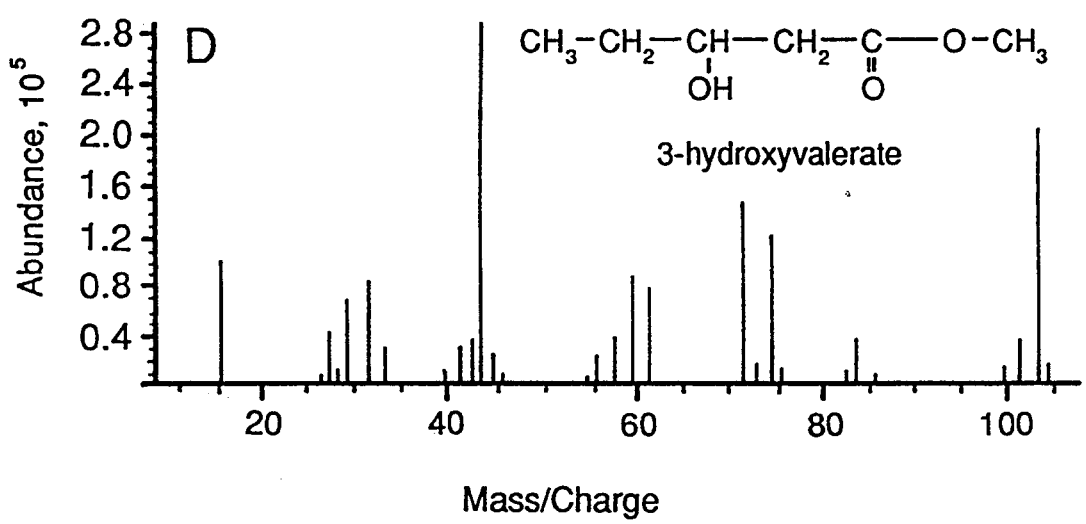

The data presented in FIG. 12 are the results of 3 sets of experiments. The data show that PHV incorporation ranged from at least about 7% to about 25%, by weight. PHV is made even at relative low levels of propionate.

While the invention has been described in terms of its preferred embodiments where a strain of transformed *E. coli* has been created which can accumulate larger quantities of PHAs while using an inexpensive carbon source such as sucrose, lactose, glucose and the like, those skilled in the art will recognize that the invention can be practiced with modification within the spirit and scope of the appended claims.

I claim:

1. A method for producing poly-beta-hydroxyalkanoate copolymers comprising:
   (a) introducing into an *Escherichia coli* host cell which expresses enzymes of acetate utilization constitutively, a vector containing a DNA sequence coding for a poly-beta-hydroxybutyrate biosynthetic pathway;
   (b) culturing the host cell on a substrate comprising a carbon source and propionate;
   (c) obtaining expression of the poly-betahydroxybutyrate biosynthetic pathway in the host cell; and,
   (d) recovering poly-beta-hydroxyalkanoate copolymers produced by the host cell.

2. The method of claim 1 wherein said DNA sequence coding for the poly-beta-hydroxybutyrate biosynthetic pathway is obtained from *Alcaligenes eutrophus*.

3. The method of claim 1 in which the vector is a plasmid.

4. The method of claim 3 wherein said plasmid is p4A which is deposited with the American Type Culture Collection *E. coli* HMS 174 and given Accession No. 68329.

5. The method of claim 1 in which the carbon source comprises glucose, fructose, sucrose, lactose, maltose or mixtures thereof.

6. The method of claim 1 in which the propionate in the substrate is present in a concentration from about 2.5 mM to about 100 mM.

7. The method of claim 1 in which the poly-betahydroxyalkanoate copolymers comprise poly-beta-hydroxybutyrate and poly-betahydroxyvalerate.

8. The method of claim 1 in which the poly-betahydroxyalkanoate copolymers comprise approximately 10–50% polybeta-hydroxyvalerate, based on total percentage of poly-betahydroxyalkanoate copolymers produced.

* * * * *